United States Patent [19]

Clyde

[11] 4,333,893
[45] Jun. 8, 1982

[54] HIGH AREA CONTACTOR

[76] Inventor: Robert A. Clyde, Alfred University, P.O. Box 486, Alfred, N.Y. 14802

[21] Appl. No.: 114,637

[22] Filed: Jan. 23, 1980

[51] Int. Cl.³ .............................................. F02M 17/28
[52] U.S. Cl. .............................. 261/94; 261/DIG. 72; 210/150
[58] Field of Search ................... 210/150; 261/94, 95, 261/DIG. 72, 96–98; 55/233

[56] References Cited

U.S. PATENT DOCUMENTS

| | | | |
|---|---|---|---|
| 2,212,932 | 8/1940 | Fairlie | 261/DIG. 72 |
| 3,589,518 | 6/1971 | Brebion et al. | 210/150 |
| 3,589,687 | 6/1971 | Leybourne | 261/DIG. 72 |
| 3,882,027 | 5/1975 | Lunt | 210/150 X |
| 3,957,931 | 5/1976 | Ellis et al. | 210/150 X |
| 4,208,284 | 6/1980 | Pretorius et al. | 261/94 X |

Primary Examiner—Thomas G. Wyse
Attorney, Agent, or Firm—Pitts & Kesterson

[57] ABSTRACT

Individual high area contactors suitable for filling a rotary biological contactor and for packing a fluid column or tower are disclosed. According to this invention each of the individual contactors include a tough abrasive-resistant outer member such as perforated substantially spherical members, or cylindrical shaped outer members such as Raschig rings. This tough outer member encloses or protects a more fragile high-area internal member or reaction support member. In a preferred embodiment such as for high temperature uses or uses where the contactor would be exposed to the ultraviolet rays of the sun, the outer member is preferably made of abrasive resistant ceramic and the high-area internal member is a ceramic sponge. In certain embodiments, the outer member can be made with a rather thin shell and still maintain its strength by the use of internal ceramic sponge shaped to provide support to the outer shell. In addition to ceramic, and for other uses, both the outer member and the high area internal member can be made of plastic like material. In other embodiments, the internal member can be made of carrageenan and resin, while in still others it may be ceramic sponge coated with a metal or other selected material. The selection of materials is dependent upon the use to be made of the contactor and the type of enzyme, reaction, etc., that is to be supported by the high-area internal members.

21 Claims, 31 Drawing Figures

HIGH AREA CONTACTOR

BACKGROUND OF THE INVENTION

This invention relates to new and unique high-area contactors suitable for use in substantially any kind of chemical or biological reaction or process wherein a substrate having a high area is needed. More particularly this invention relates to high-area contactors used in mass transfer operations and catalytic scrubbers. The contactors must also have the ability to withstand the turbulence of a fluid flowing therethrough, vibrations, abrasions and other movements which would tend to destroy or otherwise break a fragile high-area contactor.

As will be recognized by those skilled in the art, many chemical reactions such as that in an automobile catalytic convertor, as well as those which occur in gas/liquid fluid exchange packing towers require a reaction support means having a high surface area. In addition, biological processes such as enzyme reactions which might be used in sewage treatment plants on the conversion of sugars to alcohols by fermentations as well as other processes using enzymes and other biological operatives are facilitated by the use of supports having extremely high contact areas. Such biological processes may also take place in packing towers on alternately may occur in rotary biological contactors. In the past, the high area necessary for these processes has been provided substantially according to two techniques. In the first technique, a monolith member, such as for example a wire mesh, a sponge or the like substantially fills a container in which the desired reaction is to take place. Unfortunately, when such a monolith structure is used for filtering, it will be appreciated that the filter may well tend to clog with particles which are being filtered therefrom by the liquid being passed therethrough. Thus, it will be appreciated that such filters, of course, require continuous cleaning and maintenance. In addition, the use of such meshes, and sponges which are often mde of plastic or wire, cannot be used with extreme high temperatures, as the metal meshes may well tend to react with the fluid passing therethrough and the plastic sponges may simply melt. In this regard, U.S. patent applications No. 937,085 filed by Clyde et al solves the excess heating problem by making packing elements out of a ceramic sponge. Mr. Clyde's U.S. Pat. Nos. 3,900,646 and 3,998,758 described methods of plating the sponge with metals. Unfortunately such ceramic sponge packing materials do suffer from the disability of being quite fragile and subject to breaking and flaking. However, it will be appreciated that these type monolithic sponges and meshes do tend to provide a such greater amount of contact surface than do other techniques.

Also, as is mentioned heretofore such monolithic foam and mesh type support members although providing great surface area for both chemical and biological processes, will tend to clog if the process results in a precipitate. Especially in the case of the biological processes, the growth of the enzymes and microbes will quickly fill the small spaces in these type elements. It is also important to realize that although these wire mesh and sponge type elements are desirable because of their extremely light weight, once they start filling with the biomass and precipitate the weight often increases many fold.

Although it is well known that a large surface area is important in an effective gas contactor, it has also been observed that the coefficient of mass transfer from a gas to a liquid droplet is ten to thirteen times greater than from a gas to a flat surface. Thus, it will be appreciated that the use of a foam type monolith having great numbers of sharp and clearly defined points from which droplets can be produced as well as a large surface area is specially efficient.

Techniques (other than the monolith discussed above) commonly used to provide high surface area supports are the packed column technique and rotary biological contactor. According to these techniques, small individual elements which may have a particle size which ranges from small sand up to three inches in diameter are used. These elements are poured into a container to form a filter bed, distillation column or packed column. It is well understood, of course, by those skilled in the art that although small elements which might be the size of the grain of sand or smaller provide tremendous surface area for a reaction, they also provide very great resistance to the flow of the fluid therethrough. On the other hand larger elements, such as for example two or three inch spheres, although providing less resistance to the flow of the fluid do not offer near the surface area of the smaller particles. The reason that the smaller particles provide such resistance is that these particles tend to pack together such that there is little or no space left between adjacent particles. In the past, when a higher area was desired, it was customary to go to a smaller size but this increases cost and weight and decreases percentage of free space. The cost per cubic foot of ½-inch ceramic Raschig rings, for example is nearly four times that of the 2-inch size in large quantities. Further, even where spaces may remain between adjacent particles, precipitates or biological growth may quickly fill these spaces. Still another difficulty, is that the plate or support upon which the filter material or packing material rests must include perforations therethrough which are smaller than the smallest particle size. For example, a bed of sand cannot be supported by a metal plate having perforations therethrough which are greater than the smallest of the grains of sand or the sand would simply sift through the perforations. Thus, it is really appreciated that the base support itself quickly becomes one of the primary causes of resistance of a fluid through such a filter and support member. In the present invention a relatively open support plate can be used with 2-inch rings while a high area provided by the inner sponge which also promotes drop formation, has a high percentage of free space and low weight. In a distillation column, to get high purity it is especially important to have an efficient packing in the top of the column, the so-called "pinch" region of the McCabe-Thiele diagram. Excess weight in the top is a contributing factor in packing breakage in the bottom of the column. Old columns could be upgraded by simply replacing some packing in the top with a more efficient type. Consequently, to provide the desired surface area on elements having a size substantially larger than the perforations in the support plate, packing elements of various sizes and shapes are used. Such packing elements include for example, pierced hollow ceramic spheres such as disclosed in U.S. patent application, Ser. No. 39268 filed by Robert A. Clyde who is the inventor of the present invention, as well as Raschig rings, pall rings, berl saddles and Intalox saddles all of which are available from companies such as the Norton Company of Akron Ohio. The purpose of these various shapes, is of course, to provide a large amount of surface area while at the same time providing shapes that will not pack down and close up the spaces in between each element. As an example, the Norton Company produces a type of element called the Super Intalox Saddle which has a rather intricate design such as shown in the prior art FIG. 1 of the drawings. The purpose of this intricate shape is to help maintain free space in the packing bed by holding the individual pieces in position thereby reducing settling of the bed. The design is also intended to provide more interstital space and transfer points for the liquid which constantly moves across the surfaces to promote greater mass transfer. However, it will be appreciated that although such a shape is effective, the production of great quantities of such intricately shaped elements for purpose of packing a column is also very expensive. It will be appreciated that such elements as the Intalox Saddle and the Raschig ring as well as others are often made of high-impact plastic or ceramics or other hard materials which can withstand abrasion, vibrations turbulent fluid flow and the like without breaking or fracturing.

Thus, it is seen that a choice often must be made between a high-area fragile foam material or individual packing elements with much less contact surface which can withstand abrasion and abuse. There is a third choice, unfortunately it is not much better. That is, the surface area can be increased while at the same time maintaining the high strength characteristics by providing intricate shaped packing elements such as the Super Intalox Saddle. The trade off, being of course, that the Super Intalox Saddles or similar intricate shaped designed individual units are substantially more expensive than the simply shaped spheres, Raschig rings or the foam materials.

As was mentioned heretofore, one of the primary purposes of a high-area contactor is for the purpose of establishing contact between a liquid and a gas or a liquid and a biological operative. One way of accomplishing such high-area contact is by the use of the RBC (rotary biological contactor): Examples of an RBC is discussed in U.S. Pat. Nos. 4,028,244 and 3,956,127 both issued to Leaf Holmberg. According to these patents, there is disclosed a cylindrical shaped container adapted for rotation along its axis, and which is partially submerged in a liquid. The cylindrical container is for example made of wire mesh and is filled with individual items such as the plastic spherical hollow balls described in the patent. Thus, the spherical balls provide a surface for contact between the liquid and the gas or air above the rotating contactor. As the cylinder rotates, the various plastic balls are alternately exposed to the liquid and the air. In addition, column or tower packed contactors such as discussed in U.S. Pat. No. 3,796,657 issued to Pretorius et al provides a tall tower within which is packed individual element. According to this type packed column for mass transfer operations, gas-liquid contact takes place as the liquid which is usually introduced at the top of the column flows down over the packing material contained within the column at the same time the gas introduced at the bottom of the column flows upward through the column countercurrently to the liquid. The purpose of the packing material, of course, is to increase the intimacy of contact between the two fluid phases to facilitate the transfer of material from the gas phase to the liquid phase or vice versa. As was mentioned heretofore, of course, the high contact area may be provided by a porous medium such as a wire mesh or foam or may instead be made of individual elements such as Raschig rings or Intalox Saddles or other individual elements. Since several factors are involved in providing a packing column which operates efficiently, of particular importance is the selection of the packing material. Thus, the packing material should be constructed as was discussed heretofore in such a manner that it provides a minimum pressure drop across the column. Also, of course, it must be chemically inert with respect to the various phases of liquid and gas which it contacts. It should also have high mechanical durability and be able to withstand turbulence abuse and abrasion that might be experienced, while at the same time be light enough so that elements in the bottom of a high column will not break.

As was discussed heretofore, the coefficient of mass transfer of gas to liquid droplets is ten to thirteen times greater than that of a gas to a flat surface. As a result of this higher efficiency, certain packing material such as the Intalox Saddles have been designed to enhance the droplet formation. Thus, from the above, it can be seen that a great deal of time and attention has been paid in the past for purposes of finding a better way of providing a high surface area which has the strength and ability to withstand fracturing and the ability to withstand high temperature while at the same time remaining inert to substantially all possible chemical and biological reactions. For a more complete discussion of the prior art and efforts made with respect to these problems, the reader is again referred to patent application Ser. No. 937,085.

SUMMARY OF THE INVENTION

Therefore, it is an object of the present invention to provide a high-area contactor element which will not break or fracture when subjected to abrasion and fluid turbulence.

It is another object of the present invention to provide a rugged and tough high-area contactor element having a multiplicity of clearly defined sharp areas and points.

It is yet another object of this invention to provide a rugged and tough high-area contactor element having a multiplicity of sharp areas and points which elements are inexpensive and simple to produce.

Still another object of this invention is to provide a rugged tough high-area contactor having a multiplicity of sharp areas and points which contactor elements do not provide excessive resistance to a fluid flow therethrough.

It is yet another object of this invention to provide a rugged and tough high-area contactor having a multiplicity of sharp areas and points which are prevented from clogging due to the agitation of elements by tubulent fluid flow.

It is yet another object of the present invention to provide a rugged and tough high-area contactor which promotes turbulence.

It is still another object of this invention to provide a rugged and tough high-area contactor having a multiplicity of sharp areas and points suitable for use in a packed fluid tower.

It is also an object of this invention to provide a rugged and tough high-area contactor which high area can be coated with an operative such as metal, enzymes, microbes, resins or other operatives.

It is yet another object of this invention to provide a rugged and tough high-area contactor having a multiplicity of sharp areas and points suitable for use with a rotary biological contactor.

These and other objects of this invention are accomplished according to the present invention by providing high-area fluid contactor elements which are suitable for use as a support structure. By providing high areas, these support structures promote physical, chemical and biological reactions. According to this invention, these high-area contactors comprise an inner structure having a large surface area. Such a large surface area is preferably provided according to this invention by a plastic or ceramic sponge which comprises a network of randomly located interconnected closely adjacent filaments which define a plurality of interconnecting cavities. This new work of filaments and cavities accomodate fluid flow through the structure while at the same time presenting a torturous flow path. Such a high area inner member is suitable for promoting a selected physical, chemical or biological reaction by providing a contactor support surface for attaching an operative such as metals, enzymes or microbes. This high area inner structure is then protected by an outer structure which is resistant to abrasion, wear and impact in such a manner that the lower structure is accessible to fluid while at the same time being protected from the abrasion, wear and impact. According to certain embodiments of the invention, the inner structure, can be selected to have a shape which provides significant strength to the outer structure. Thus, the shell or thickness of the outer structure may be made substantially thinner than would otherwise be possible. Fiberglas can also be put into the outer shell for increased strength. According to a specific example of this invention, a cylindrical shaped member commonly referred to as a Raschig ring and having a thin shell provides protection to a recessed ceramic sponge having a selected form. High-area contactors of this invention such as a Raschig rings with a ceramic inner member which provide support to the outside Raschig ring as wall as a high surface area are particularly suitable for use in both rotary biological contactors, packed fluid towers, and distillation columns.

DETAILED DESCRIPTION OF THE INVENTION

Figure 1:
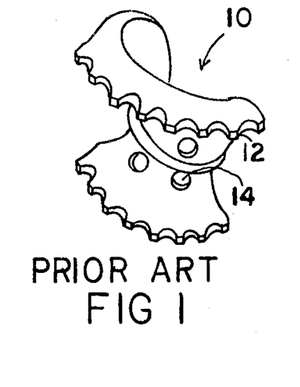
FIG. 1 shows a prior art fluid packing tower element showing the intricate shape of the Super Intalox Saddles.
Figures 2A, 2B:
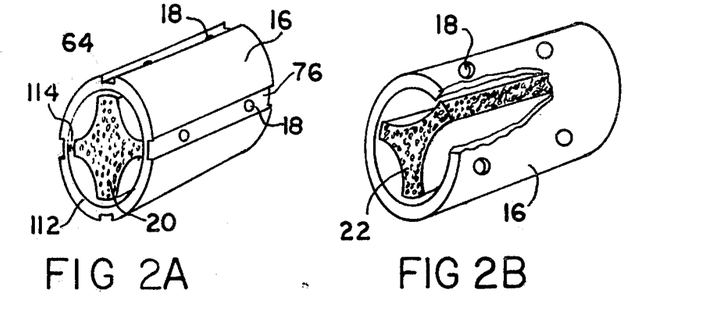
FIGS. 2A and 2B are preferred embodiments of the present invention showing a selected protective outer member and an inner high area contactor sponge member which also provides support.
Figure 3:
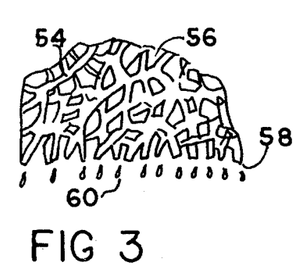
FIG. 3 is a close up of a section of the inner member sponge of the various figures showing the formation of liquid droplets.
Figures 4A, 4B:
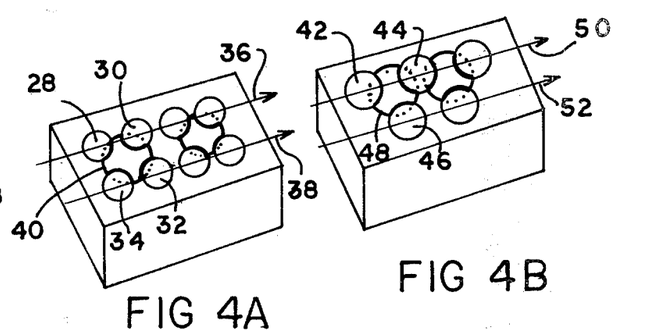
FIGS. 4A and 4B illustrate how ring-shaped, four-prong shaped and three-prong shaped sponge members may be formed with minimum waste.
Figure 5A:
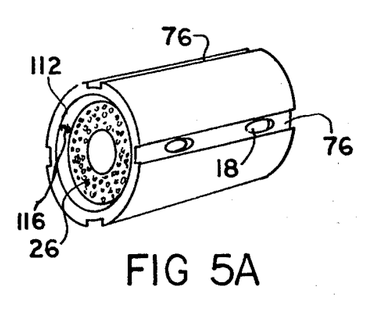
FIGS. 5A through 5D show additional arrangements of the inner ceramic sponge designed for providing high area and low resistance to fluid flow, as well as strength to the outer cylindrical ring.
Figure 5B:
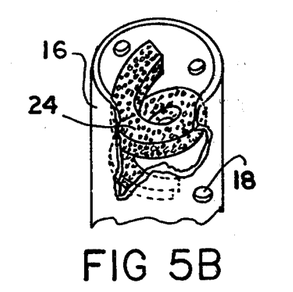
Figure 5C:
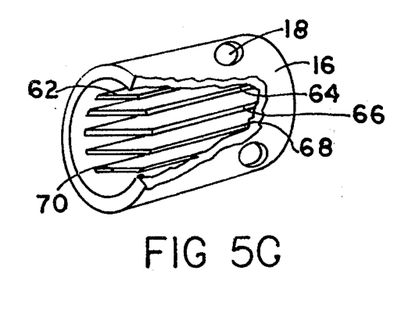
Figure 5D:
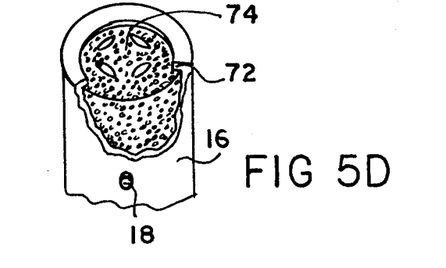

As was discussed heretofore, individual elements used in fluid packing towers for providing a contact surface between gases and liquids for purposes of accelerating physical, chemical or biological reactions, is well known. Presently, one of the better known prior art packing elements is the Super Intalox Saddles made by the Norton Corporation. Referring now to FIG. 1 there is shown a perspective view of this prior art packing element. As can be seen from FIG. 1, the element as shown generally at 10 is of an unusual saddle shape, includes a multiplicity of scallops 12 shown on at least two of its edges, and also includes a multiplicity of holes 14 located on the body of the element. This particular element has been designed so that two like elements (that is two Intalox Saddles) cannot nestle too closely to each other. Thus, according to this prior art element there is always maintained a substantial amount of space between two of the elements even when the elements are in contact with each other. However, a casual observation of the prior art element of FIG. 1 immediately reveals the intricacy of the element and suggest the difficulty experienced in manufacturing such an element. Thus, it will be appreciated that since thousands or millions of such elements might be necessary in a large packed fluid column the expense of these elements even when costing only a few cents each can be exorbitant. Therefore, referring to FIGS. 2A, 2B, 5A through 5D, 8A through 8D, 11A and 11B, there are shown individual contactor elements incorporating the features of this invention which provide for a substantial cost savings in the manufacturing of the elements, and at the same time provides even better contact surface area and void space. As can be seen from the embodiments shown in FIGS. 2A, 2B, and 5A through 5D, all of the elements shown are substantially of a cylindrical shape. A basic cylindrically shaped individual contactor element has been used in packing columns in the past. These elements were identified as Raschig rings. However, as is well known by those skilled in the art the basic and well known Raschig ring was simply a plain cylindrical shaped member. The simple 2" Rashig ring from the Norton Company has a wall thickness of ¼ inch to withstand the pressure from the ring above it touching at only one point. As will be discussed hereinafter, a convoluted outer wall results in contact at two or four points so there is less pressure and the wall can be thinner reducing the pressure on the packing in the bottom of a tall column. Referring now to FIG. 2A there is shown one of the preferred embodiments of the present invention. Acording to this embodiment a basic cylindrically-shaped member 16 includes a multiplicity of holes 18 through the shell of the ring 16. Cylindrically-shaped member 16 may, depending upon the intended use of the packing column and the fluids which the ring will be exposed, be made or fabricated from any suitable material such as plastic, nylon, vinyl, polypropylene, ceramic and the like. Located inside cylinder 16 is a shaped foam member 20 which provides an extremely high area contact surface. As can be seen from FIGS. 2A through 5D, the shape of the interior high-area contactor member can be of substantially any selection and design. However, it is believed that the cross shaped member 20 of FIG. 2A and the 3 prong member 22 of FIG. 2B provides unusually effective fluid flow, surface area and strength. The use of such shaped members provides reinforcement to the cylinder 16 such that the cylinder walls may be substantially reduced in thickness and thereby further reduce the weight of the element. It has also been found, that the shape of the inner/high-contact member 20 of FIG. 2A, 22 of FIG. 2B and 24 of FIG. 5B are especially useful for larger diameter outer members. In a similar manner, the ring shaped inner high-contact member 26 of FIG. 5A has been found effective for smaller diameter units. As will be discussed hereinafter with respect to the technique of manufacturing and forming the elements shown in FIGS. 2A through 4A, mass production of the unit can be achieved at substantial savings by complete utilization of raw materials used in forming the interior high-area contact members. For example as will be come clear hereinafter, the foam interior when made of a plastic sponge or ceramic sponge which is in turn derived from a plastic sponge, can be achieved by cutting the ring-shaped sponge members 26 shown in FIG. 5A, which are used in small diameter elements from a block of sponge material, such as shown in FIGS. 4A and 4B. As is shown the holes 28, 30, 32 and 34 in FIG. 4A represent cylindrical portions of the sponge removed for use in the units of the type shown in FIG. 5A. According to this FIG. 4A, it can be seen that the various holes or the cylindrical portions which have been removed are in a regular pattern. That is, the holes in row 36 are parallel and aligned with the holes in row 38. As can be seen, and as is indicated by the darkened outlined area 40, there is formed a cross-shaped member which is suitable for use as the cross-shaped member 20 of FIG. 2A. In a similar manner, by removing cylindrical portions indicated by holes 42, 44, and 46 as shown in FIG. 4B, it can be seen that a three-pronged member such as is outlined by the dark area 48 can be achieved. The three-pronged effect is achieved by having a staggered relationship between the two parallel rows of holes 50 and 52. Thus, it will be appreciated that by staggering the parallel holes the resulting centerpiece can be a three-pronged member such as indicated by member 22 of FIG. 2B. Another very simple and effective way of providing the high inner-surface area to the interior of the protective cylinder, is shown in FIG. 5B. According to this technique, a strip 24 of waste sponge is simply forced into the cylindrical member. Elasticity holds it against the side. In this technique, the strip 24 will typically take on a spiral shape within outer member 16. FIGS. 5C and 5D show still other arrangements of tough rugged abrasive resistant outer cylindrical shells 16 used to protect the inner sponge member. Also, the arrangement of the inner surfaces shown in FIGS. 5C and 5D can be used for other types of supports, these arrangement will be discussed further hereinafter. Referring now to FIG. 3, there is shown an enlarged section of a portion of sponge that might be used in the various arrangements shown in the figures already discussed as well as other embodiments described hereinafter. In the past, packing materials were designed with as large a surface area as possible in order to provide a film of liquid for the gas to contact since it was believed that the most efficient mass-transfer could take place in this manner. However, as was discussed heretofore, it has been observed recently that the coefficient of mass-transfer from a gas to a liquid droplet is 10 to 13 times greater than from a gas to a flat surface. (Perry's Chemical Engineering Handbook, 5th Edition, Section 18, Page 42.)

The enlarged view of the sponge used in the FIGS. 2A through 5D as shown in FIG. 3 illustrates the various voids 54 and the interconnecting filaments 56 typical in such a sponge. Along lower edge 58 there are shown the broken and sharply defined points from which various droplets 60 of water fall. It will be appreciated as a liquid flows through a sponge-like material and off at its edges, a great number of such liquid droplets are formed because of the many and multitude of sharply defined points.

Although the high-area contactor of this invention is suitable for being fabricated from many various materials, depending upon the application and the type of reaction to be supported, it will be appreciated that the features of this invention are particularly suitable for use with ceramic type contactors. The ceramic can comprise crystalline types such as porcelain, mullite, alumina, zirconia, zircon, cordierite, fosterite, spodumene, perovskite, steatite, magnesia, silicon carbide, silicon nitride, beryllia and the like, as well as the glassy types such as borosilicates, sodalime, flint, plate, alumina silicate, silica (quartz) and the like. Perovskite is particularly valuable because it will take a small electric charge and can thus be useful in waste treatment. For example, it will be appreciated that the cylindrical outer members such as shown in FIGS. 2A, 2B, 5A, 5B and 5C are particularly suitable for being made from a ceramic material. For example, if the exterior were to be made from a hard, tough plastic material and the interior high contact member 20, 22, 24 and 26 were to be manufactured from a soft sponge it can be seen that the outside member provides substantially all of the support since the inside soft member could not provide support. However, if the outside member is made of a tough ceramic and the inside high-area contactor members are made from a ceramic sponge it will be appreciated that the inside members such as shown in 20, 22, 24 and 26 of FIGS. 2A, 2B, 5A and 5B respectively, will provide substantial support to the outside member since they will be rigid. Thus, when used with ceramic, the outside members 16 can therefore be made with a substantially thinner cylindrical shell which means less weight, and the resulting less pressure on the bottom elements in a high column. On the other hand, it should be noted that the configuration shown in FIG. 5C although suitable for being made out of a ceramic material, and having sheets 62 through 70 made out of sheets of ceramic foam, such a configuration as shown in FIG. 5C is unusually suitable for use with sheets of carrageenan coated ceramic or plastic and nylon for providing a contactor surface. Carrageenan which provides an unusually good surface or matrix for the growth of enzymes and microbes, as is known in the art, is a fragile substance that cannot withstand abrasion or impact and must be protected. Thus, the structure shown in FIG. 5C is ideally suited. In addition to ceramic, a plastic element can also be coated with carrageenan as well as a biological operative.

Figure 6:
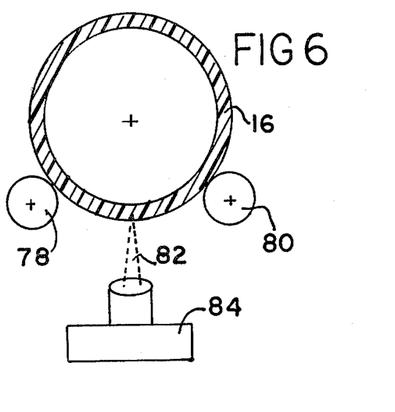
FIG. 6 shows a laser beam technique for providing holes in a Raschig ring such as shown in the figures.

On the other hand, the structure shown in FIG. 5D is ideally suitable for a plastic or nylon outer shell 16 and a foam sponge interior member 74. The outer shell can also be injection molded and can comprise high impact polypropylene, Teflon TM, polyvinyl chloride, polyethylene, Ryton TM (a high temperature corrosion resistant plastic by Phillips Petroleum) or the like. The inner high surface area member can comprise polyurethane, polypropylene, fiberglas, teflon or a net such as is used to hold fruit or wash dishes. It is believed that a particularly useful non-ceramic member can be obtained by forming a Ryton TM outer shell (which may be cylindrical or a scalloped cylinder) and packing the outer shell with a "Teflon curl" as shown in FIG. 5B. The term "Teflon curl" refers to waste material which results from the machinery of Teflon, such as by a lathe, just as waste metal curls occur when metal is machined. The "Teflon curl" can then be held in place by spraying the Ryton shell and Teflon curl with just enough suitable solvent so that there is adhesion between the two. Alternately, the curl can be held in place by wrapping a Teflon thread around the two open ends of the cylinder. As can be seen from this embodiment, exterior member 16 also includes a lip 72 for retaining the foam inner-structure 74. As can be seen from all of the embodiments discussed heretofore, it may be particularly desirable to include apertures 18 therein. When punching the aperture a projection can be formed which holds the inner sponge. These apertures may be produced in the outer shell 16 at any time during fabrication. It has been found however, that by providing a groove 76 along the outside cylindrical member as is shown in FIGS. 2A and 5A, and in a location such that the holes 18 are located in such a groove, there is substantially improvement of the channeling of liquid from the outside of the member to the inside such that greater contact with the foam material inside results. This groove also results between a lower element, and the one above. Although the apertures 18 may be provided in the cylindrical members according to any suitable technique including punching with small needles or cutters, it will be appreciated that providing holes in fired ceramic may be particularly difficult. Therefore, referring now to FIG. 6 there is shown a suitable method for providing the apertures in fired ceramic. According to this figure, the cylindrical-shaped outer member 16 is placed upon a pair of rollers 78 and 80 such that the cylindrical member may be rolled to expose different areas to the laser beam 82 provided by a laser means 84.

As was discussed, however, the apertures may be provided by any other suitable technique. It will be appreciated that cylindrical members may be made out of nylon, plastic, polyurethane and the like as well as unfired ceramics by an extruding process. That is, the cylindrical shape results by extruding the material by force through a mold. Further, it will be appreciated that as the cylindrical shape is extruded needles or "V" shaped cutters in the mold may be provided as is shown in FIG. 7 to provide the aperture. It will be appreciated that it is not necessary to stop the extruding process as the needles or cutters are lowered into the material to avoid elongated holes. In fact it has been found that such elongated holes in the material provide better flow of liquid to the interior of the cylindrical members. Thus, so long as the elongated holes do not extend to the edge or end of the cylindrical members, this type process is particularly suitable. It has further been found that in forming the apertures, the material removed from the aperture will not usually be completely removed, but will usually remain as excess material located around the aperture and projecting into the interior of the cylindrical-shaped element. It is not necessary to remove such excess material, and in fact, it has been found that such excess material penetrating to the inside of the element provides clearly defined points such as point 85 of FIG. 8D helps to produce droplets of liquid, and prevent the liquid from simply running around the inside wall of the element. The excess material also helps hold the inner sponge in place such that a lip 72 such as discussed heretofore with respect to FIG. 5D is not necessary.

Figures 7A, 7D, 7E:
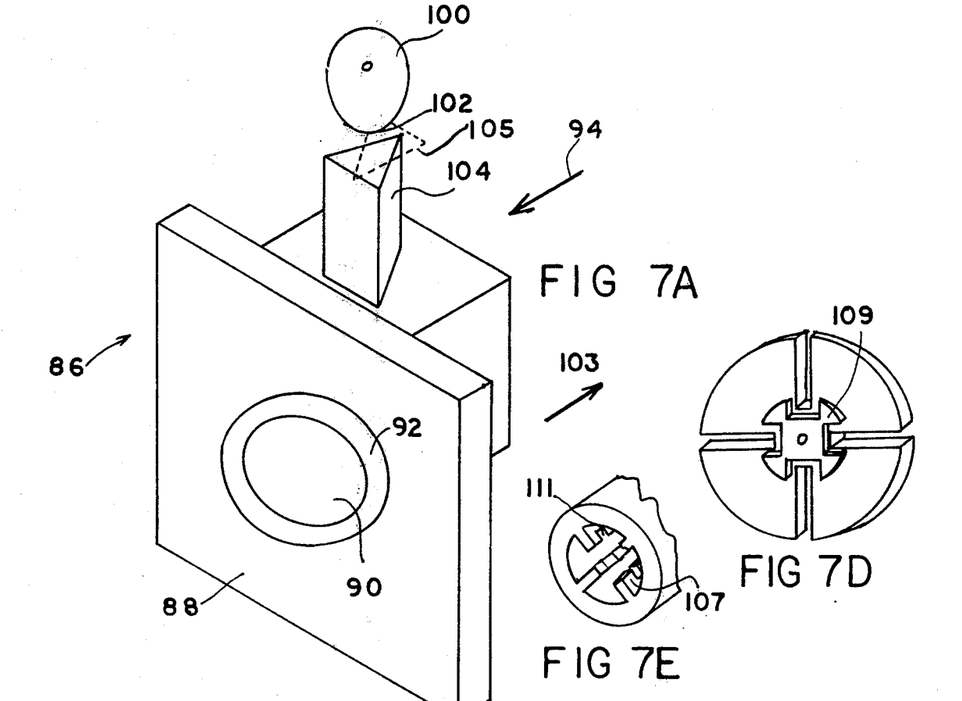
FIGS. 7A through 7E illustrate how an extrusion die may include a suitable "V" shaped cutter to form holes in the cylindrical-shaped members.
Figures 7B, 7C:
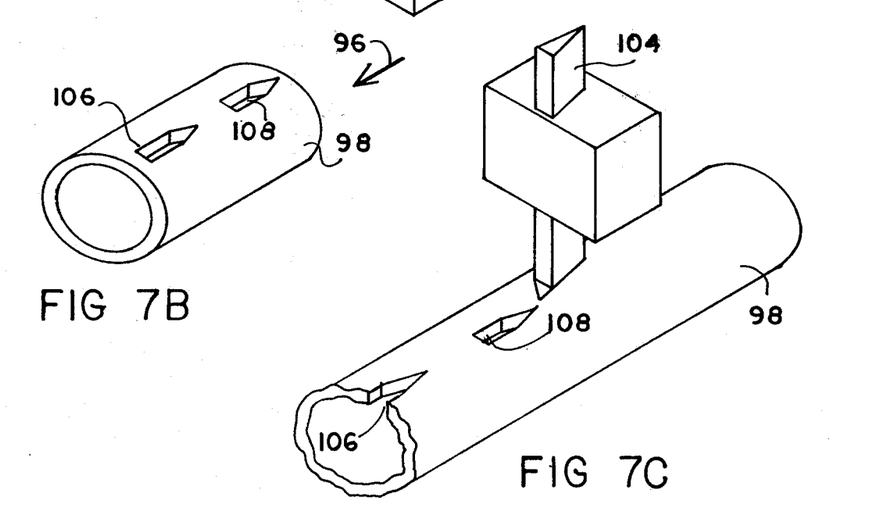

Referring now to FIGS. 7A, 7B and 7C there is shown an example of how the holes may be cut into material being extruded. As shown extruding die 86 includes an outer member 88 and an inner member 90. The material to be extruded is forced through annular apparatus 92 in a direction indicated by arrows 94 and 96 thereby producing a tube-like extrusion 98 of the extruded material. As the material is forced out of the annular ring, cam 100 may rotate at a selected frequency such that end 102 forces "V" shaped cutter blade 104 through the tube shaped material to form apertures 106 and 108 as shown in the figures. FIG. 7C is shown without the die to better illustrate this process.

Figure 8A:
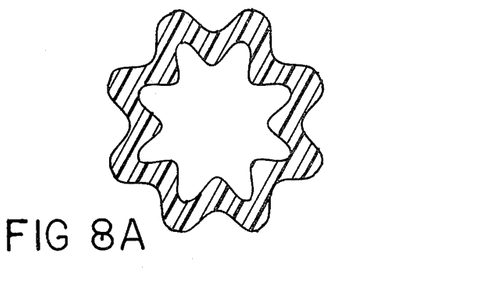
FIGS. 8A through 8E show other cylindrically outside rigid members similar to the Raschig ring, but having a scalloped cross-section and incorporating the features of this invention.
Figure 8B:
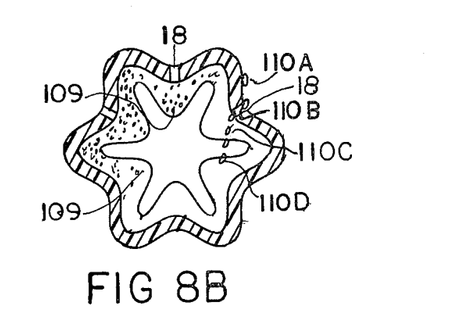
Figure 8C:
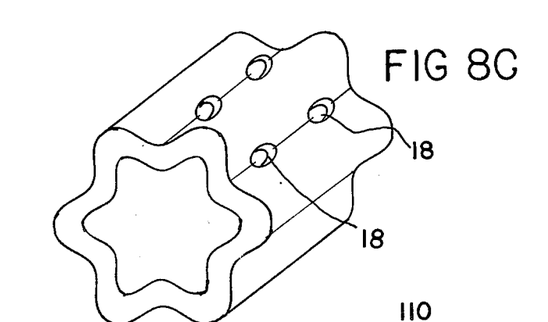
Figure 8D:
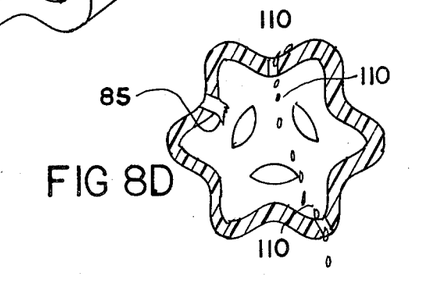

It will be appreciated, however, that to form the points 85 such as shown in FIG. 8D, it is necessary for holes to be formed after the extrusion process. Therefore, referring now to FIG. 7A, 7D, and 7E, it can be seen that if the material to be extruded is forced through the annular ring 92 in a direction indicated by arrow 103, then the cutter blade 104 will form the operation after the hole is extruded. It will also be appreciated that cutter blade 104 will preferably be rotated 180° as indicated by dotted line 105 such that the sharp edge of cutter 104 will be effective. FIG. 7D illustrates how internal ribs 107 shown in FIG. 7E can be formed during the extruding process by modifying the die by adding slots. FIG. 7D also illustrates how a rotating cutter wheel 109 can be mounted to the die to put indentations 111 on ribs 107 to facilitate the formation of liquid droplets.

In addition to cylindrically-shaped outer members 16 shown in the figures, it will be appreciated that other substantially cylindrical members such as the scallop-shaped cylindrical members 8A, 8B, 8C, 8D and 8E shown in cross-section are also particularly useful in this invention. Outer members having such a scallop-shape have been found useful in that the flow along the valleys directs liquid from the interior of the outer member through holes 18 to the high surface contact inner member. It will also be appreciated that the scalloped shaped members shown in the cross sctions 8A through 8E may readily be fabricated by the extrusion process. Likewise, either by using sharp needles, "V" shaped cutters or a laser beam the necessary holes 18 as shown in FIG. 8C can be provided.

Figure 8E:
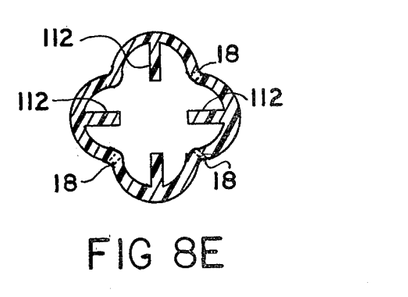

Referring now particularly to FIG. 8E, there is shown a scalloped outer member which is believed to provide a particularly useful shape for use with this invention. It should particularly be noted that the crest of the scallop-shape is wider than the trough so that the crest cannot fit into the trough of an adjoining element and block the holes. Investigation indicates that significant advantage over the plain Raschig ring is obtained by the scalloped shape of this invention such as shown in FIG. 8A without an inner sponge member. However, if an inside sponge member is to be used, the inside member may also have substantially a scalloped shape which matches or conforms to the outside member but as shown in FIG. 8B is designed so that the inward pointing portions 109 are thicker than the outwardly extending portion, thereby resulting in a star shaped aperture. This arrangement helps to increase the formation of more liquid droplets. That is, a liquid drop 110A passes through aperture 18 and passes through the sponge as shown at 110B and 110C. Gravity then makes the drop fall from the ceramic sponge as shown at drop 110D.

It will be appreciated that without the star shaped aperture, the liquid drop would simply run through the sponge as shown in FIG. 8D. Thus, the star shaped aperture formation is believed to result in the formation of more droplets.

With respect to all of the embodiments of the outer members heretofore discussed (having a substantially cylindrical shape) it will be appreciated that elements with a ceramic outer shell and a foam ceramic inner high-contact member are preferrably provided with a recess for the foam material so that the edge of another outer member cannot reach to the inside ceramic foam member. This is because the inside foam ceramic is fragile and can be easily broken. Thus, as is shown clearly in FIGS. 2A and 5A it can be seen that the ceramic foams 20 and 26 respectively are recessed from the edge 112 of the outer member a distance as indicated by arrows 114 and 116. As will be seen herinafter, with respect to FIG. 16 recessing the ceramic foam insert 20, prevents the edges of other cylindrically shaped members from impacting and abrading the ceramic foam.

As is well known by those skilled in the art, gelatin and yeast can be sprayed onto ceramic or plastic and cross linked with glutaraldehyde or formaldehyde-formamide. This coating is not strong enough to withstand continued abrasion, however, and could best be applied on the inside protected part of the packing. Ceramic can have a wash coat applied to increase surface area as described in SAE paper 730276 and in "DISPAL M" presented by Robert Butler at the 24th Pacific Coast meeting of the American Ceramic Society Nov. 2, 1971. In this case too, the wash coat should be protected from abrasion.

In some cases, the sponge holes may become clogged and another design would be to extrude solid strengthening ribs 112: (as shown in FIG. 8E) extending from the outside and terminating near the center.

Figure 9:
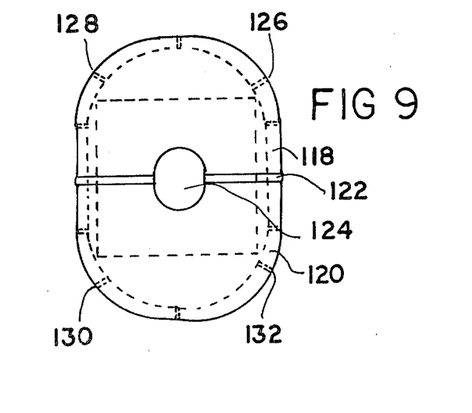
FIG. 9 shows an oval-shaped outside rigid member suitable for incorporating the features of this invention.

Referring now to FIG. 9, there is shown still another embodiment of the present invention. According to this embodiment, the outside hard protective member is substantially an oval shape or an egg shaped member having one or two large apertures. Internal to the hard outer protective member, there is included, as was in the case with the cylindrically-shaped member, a high-contact area inner member such as plates similar to those of FIG. 5C or a ceramic sponge. The oval-shaped members shown in FIG. 9 are typically made of two halves or hemispherical-shaped members 118 and 120 which are bonded together in the center portion 122. In addition to the large apertures 124, this embodiment may also include a multitude of small holes such as shown at 126, 128, 130 and 132.

Figure 10:
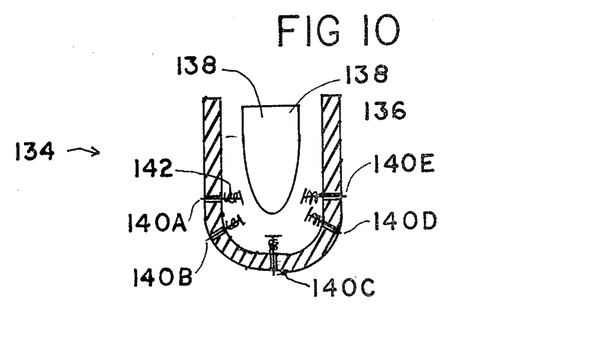
FIG. 10 shows a technique of providing holes in one-half of a spherical or egg-shaped outer member of the type shown in FIG. 9.

In manufacturing the oval or egg-shaped outside protective member as shown in FIG. 9, techniques already familiar to those skilled in the art are available. However, one particular technique is to use a liquid absorbent mold having a substantially hemispherical shape. The wet or green ceramic slurry may then be pushed into or molded around the absorbent mold such that liquid is absorbed from the green ceramic and the green ceramic dried to the point that it will maintain its shape. Once dried, each of the hemispherically-shaped members may then be provided with a multiplicity of holes or apertures while the ceramic is still green. To accomplish this, piercing structure 134 such as shown in FIG. 10 has an outside surface 136 which has substantially the same size and shape as the inside surface of the hemispherical green ceramic member. Piercing structure 134 is placed inside the green ceramic hemisphere and then the member 138 is forced downward to force the needelpoints 140A, 140B, 140C 140D and 140E against the biasing springs 142 out through the member 136 and through the green ceramic member. A polyurethane foam which has been soaked in ceramic slurry and then squeezed to remove excess ceramic slurry, may then be placed in the inside of one of the hemispherically-shaped outer green ceramic members. It will also be appreciated of course, that ceramic plates as well as other types of high area contact support member may be placed inside the hemispherical-shaped members. A similar hemispherical-shaped member is then used as a cap to enclose the inside high-area contact members. A bead 122 of wet green ceramic is placed at the juncture of the two hemispherical-shaped outer members and the entire structure then fired to achieve a hard outer ceramic shell having a multiplicity of holes, which hard outer shell encloses a fragile high-area contact inner member. The mold can of course be made of plaster, however, particularly inexpensive and simple method of manufacturing the hemispherical ceramic outer shells is to use the paper base type egg carton as the mold member. Egg cartons are easy and inexpensive to obtain, and the paper base can readily absorb the excess liquid necessary to dry the ceramic to the point that it is self-supporting, or hold the ceramic until the paper is burned off.

Figures 11A, 11B, 12, 13:
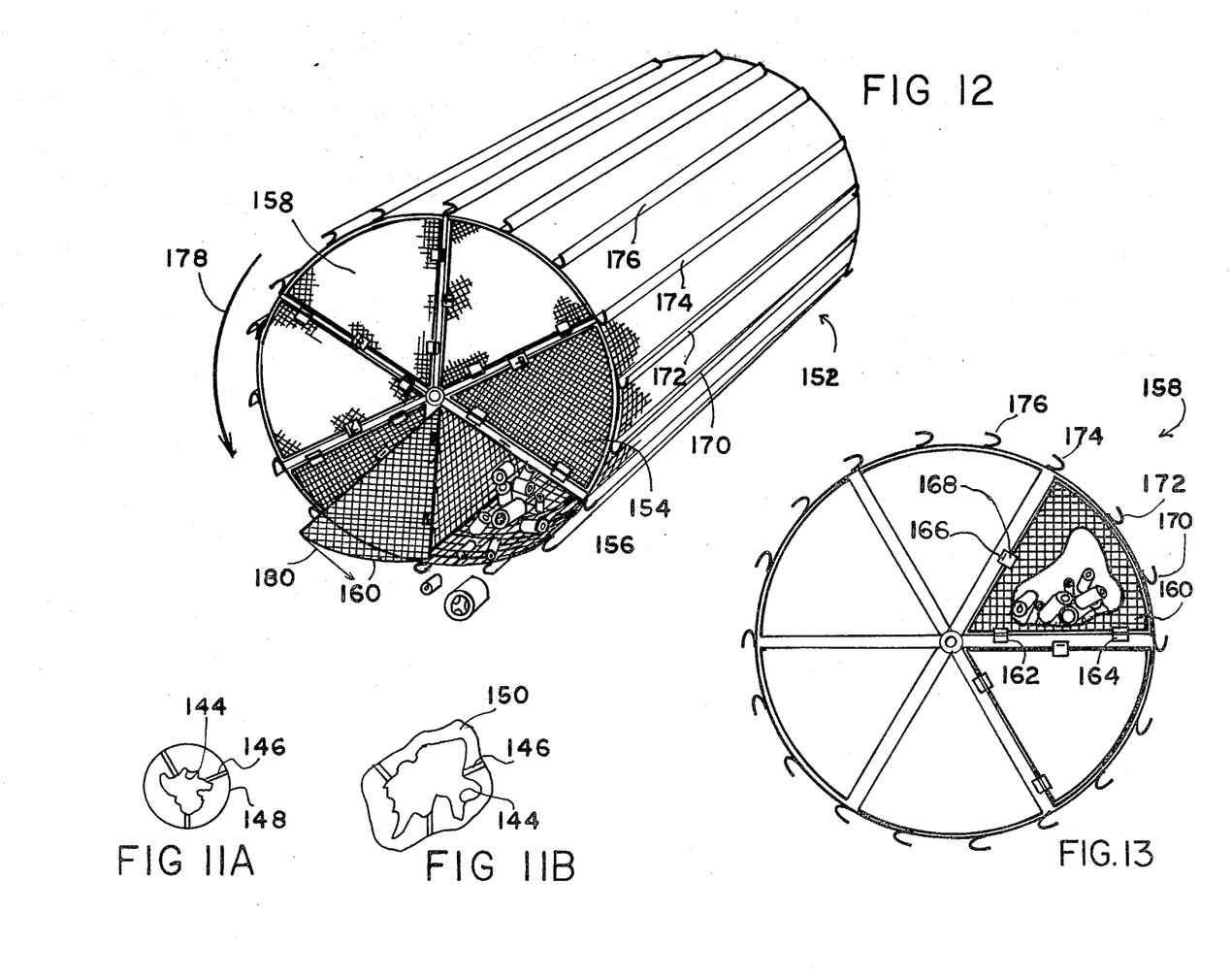
FIGS. 11A and 11B are partially cross-sectional, partially perspective views of high-area contactors uniquely made with the use of popped corn as a substrate prior to firing the ceramic.
FIG. 12 shows a perspective view of a new rotary biological contactor suitable for use with the high-area contactor elements incorporating the features of this invention.
FIG. 13 shows an end view of the rotary biological contactor of FIG. 12.

Referring now to FIGS. 11A and 11B there is shown still another very inexpensive and excellent way of providing a high-area contactor having a hard durable outer surface and a high-area inner surface. According to this technique, it has been found inexpensive and quite satisfactory to use "popped corn" as a base or mold member. The popped corn is coated with a layer of liquid or ceramic slurry, and is then partially dried. The resulting green ceramic coated piece of popped corn may then be punctured in several areas according to any suitable technique including lasers, needles, etc., and then the whole structure fired. The popped corn is an organic material, and the high heat of firing the ceramic results in the piece of popped corn vaporizing and being removed from the center such that the center of the resulting member has an extremely large surface area due to the natural convolutions and curves and surface area present on a piece of popped corn. FIG. 11A shows the resulting structure which has an inner convoluted surface 144 and aperture 145 when enough ceramic slurry is used such that the exterior surface 148 is substantially spherical. FIG. 11B shows the resulting contactor when the outside surface 150 of the coating of ceramic slurry is thin enough to follow the basic contour of the popped corn.

Referring now to FIGS. 12 and 13, there is shown a new and unique "rotary biological contactor" which is particularly suitable for use with the high area contactors of this invention discussed heretofore. As shown, the rotary biological contactor is shown generally at 152. From the disclosed embodiment of FIGS. 12 and 13, it can be seen that there are six pie shaped compartments in the contactor each completely made up of a screen mesh 154, which mesh has openings as large as possible while still retaining the high-area contactors 156. One end 158 of rotary biological contactor 152 illustrates that each of the pie-shaped sections may include a door 160 having hinges 162 and 164 and a hasp 166. Thus, by removing the retaining key 168 from hasp 166, the door 160 can be opened to provide access to the high-area contactors within. It will be noted that of the squirrel-cage type rotary biological contactor blank there are multiplicity of channels such as shown at 170, 172, 174 and 176.

Thus, in operation it will be appreciated that each of the individual pie-shaped sections will be partially filled with high-area contactors of any suitable type such as has been discussed heretofore. In addition, high-area contactors of a type disclosed in applicants copending application Ser. No. 39,268 which are pierced hollow ceramic shells are also suitable. In operation, such a rotary biological contactor is typically partially submerged in a fluid which is to be treated. Thus, as the contactor rotates as indicated by arrow 178, various pie-shaped sections of a rotary biological contactor rotate in and are alternately exposed to water and then to air. It will be appreciated by those skilled in the art, such alternate exposure to the liquid being treated and air provides the maximum conditions for growth of microbes and enzymes necessary to treat the liquid. It is also of particular importance to note that if the pierced ceramic spheres are used as a rotary biological contactor, different sizes and shapes and weights may be used such that the spheres do not settle in one location, and are continually abrading and impacting each other such that they knock loose and dislodge any enzyme and microbe growth. In addition, the channels 170, 172, 174 and 176 are used such that they collect water as they come out of the water, and then tend to pour the liquid over the high-area contactors thereby providing additional cleansing of each of these individual items. At times however, it will be appreciated that despite the self-cleaning features of the rotary biological contactor of this invention, certain types of the high-area contactors will still become fully filled and overloaded with enzymes and biological microbe growth. In such instances, the hinged door 160 is simply opened as shown by arrow 180, and the biological contactors shoveled out and replaced with new elements. The microbe or enzyme overloaded elements, are then placed in a furnace or other heating source for heating. Once sterilizing and cleaned the biological contactors are suitable for reuse. Thus, it will be appreciated that there has to this point been described a unique rotary biological contactor which is particularly suitable for using the high-area individual contacting elements heretofore described.

Figures 14, 15A, 15B:
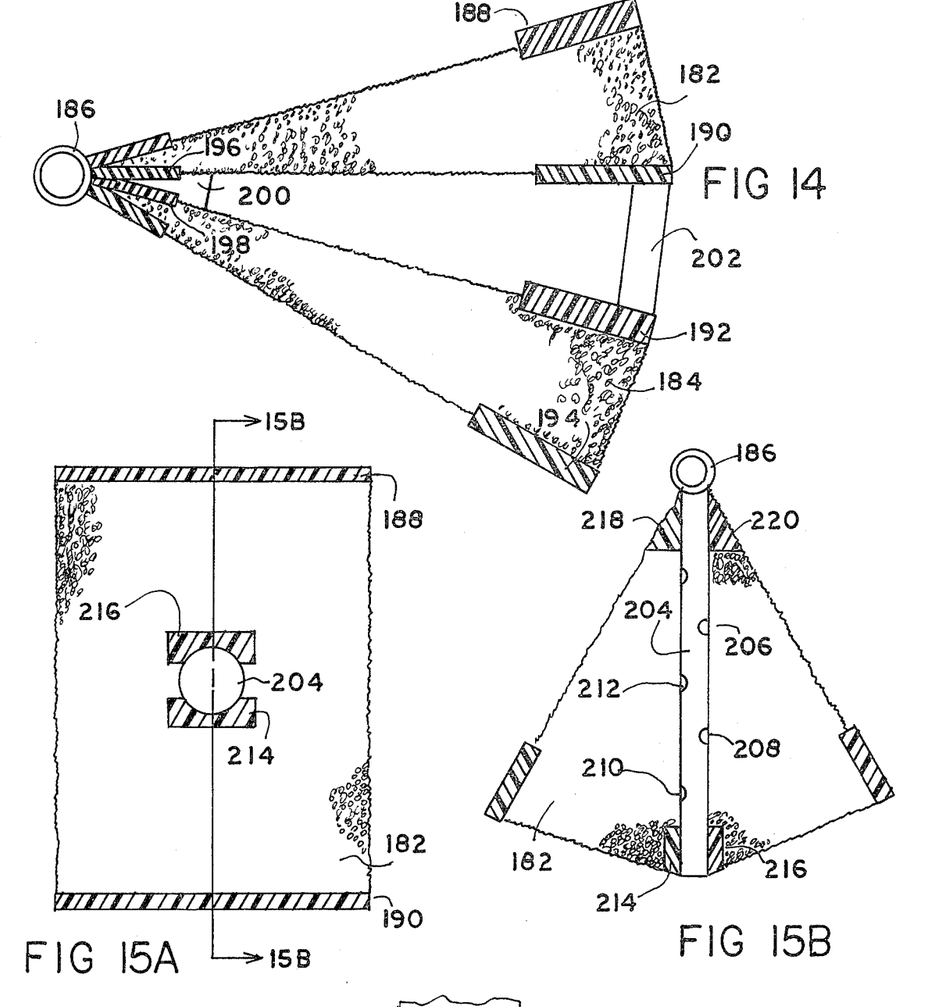
FIG. 14 shows a partial end view of a new rotary biological contactor using a multiplicity of sections of a ceramic sponge, which sections include solid ceramic support portions.
FIGS. 15A and 15B show the rotary biological contactor of FIG. 14 with means for cleaning the particles and sediment from the sponge by air or a stream of water.

Referring now to FIGS. 14, 15A and 15B, there is shown still another unique rotary biological contactor. The contactor as shown in FIG. 14 uses pie shaped sections 182 and 184 which are made of a ceramic foam. Each of the sections is attached to a hub 186 and each section includes support areas 188, 190, 192, 194 and 198 of solid ceramic. Between the multiplicity of ceramic foam sections, are support structures 200 and 202 which may be made of solid ceramic or preferably of a hard rubber-like material. However, as was the case with the rotary biological contactor of FIGS. 11A and 11B, as the ceramic foam contactor rotates, liquid which has seeped in voids of the ceramic sponge material is lifted out of the liquid into the atmosphere. This liquid then tends to run out of the ceramic sponge back into the water. It is well known by those skilled in the art that the constant exposure of the liquid to air is particularly suitable for encouraging the growth of microbes and enzymes. Thus, the ceramic sponge contactor discussed in FIG. 14 is particularly suitable for such rotary biological contactor use.

Referring now to FIGS. 15A and 15B there is shown a particularly embodiment of the contactor of FIG. 14 which includes the improvement of a perforated air or water path 204 which leads from the hub point 186 to the outside perimeter of the pie-shaped section. This arrangement is more clearly seen in FIG. 15B. As can be seen in FIGS. 15A and 15B, liquid under pressure, or air pressure may be forced through the pathway 204 and out of the apertures 206, 208, 210 and 212 thereby cleansing, scouring or otherwise removing the enzyme and biological growth from the ceramic sponge. Also, as is shown in FIG. 15B it is desirable to include reinforcement points 214, 216, 218, and 220 which are preferably made out of a solid ceramic material. Thus, according to the rotating biological contactor discussed heretofore, it will be appreciated that the sponge only contacts the liquid and the support points. Such limited contact reduces the likelihood of breakage.

Figure 16:
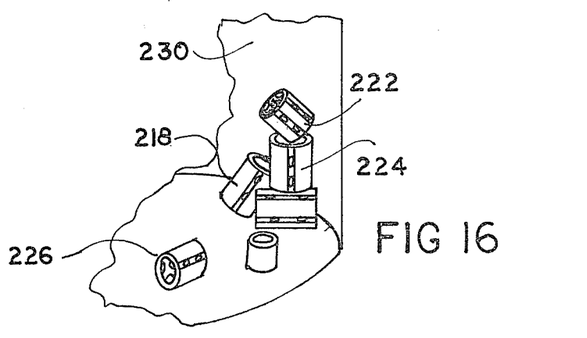
FIG. 16 shows a portion of a fluid packing tower containing samples of the high-area contactors of this invention.

Referring now to FIG. 16, there is shown a break out portion in perspective of elements in a fluid packing tower. As can be seen, a plurality of elements 222, 224, 226 and 228 are poured into the container and may fall and dispose themselves in substantially any configuration. However, as is shown with respect to elements 222 and 224 some of the elements will tend to center such that their edge penetrates to the interior of another element. Therefore, it will be appreciated that as the liquid runs through the packed column tower 230 and as the gases flow upward through the column, the inner sponge high-area contact members of the various packing elements provides significantly increased surface area as well as points for the formation of droplets so that the mass-transfer between the gas and liquid is significantly improved over such elements of the prior art. Further, it will be appreciated that because of the cylindrical outer shape of the packing elements the spaces in between the various elements are kept to a minimum and in addition packing or settling due to breakage is also kept to a minimum because of the great strength of the cylindrical shape and the reinforcement of the members. In addition, if scalloped-shaped cylindrical numbers are used breakage will be reduced because of the decrease in pressure due to contact at more than one point between one element and the one above.

Therefore, while there have been described what are at present considered to be preferred embodiments of this invention, it will be obvious that those skilled in the art that various changes and modifications may be made therein without departing from the invention, and the invention is, therefore, intended to cover all such changes and modifications as fall within in the true spirit and scope of the invention.

I claim:

1. A tough and abrasive resistant high-area fluid contactor element comprising:
   a high-area inner sponge member having a network of randomly located inter-connected closely adjacent filaments which define a plurality of inter-connecting cavities and which present a torturous flow path; and
   a tough, rigid, and abrasive resistant substantially cylindrical shaped outer member surrounding said inner member to protect said inner member from abrasion and impact, said outer member having a first selected length and a first and further end.

2. The fluid contactor element of claim 1 wherein said high-area inner member is a sponge selected from the group consisting of ceramic and plastic.

3. The fluid contactor element of claim 1 wherein said sponge has a second selected length, which second selected length is less than said first selected length such that said sponge is recessed a selected distance from said first and further ends of said cylindrical-shaped outer member.

4. Fluid contactor element of claim 3 wherein said sponge inner-member has a cross-shaped cross-section.

5. The fluid contactor element of claim 3 wherein said inner-sponge member has a triangular-shaped cross-section.

6. The fluid contactor element of claim 3 wherein said sponge inner-member has a ring-shaped cross-section.

7. The fluid contactor element of claim 3 wherein said sponge inner-member has a star shaped aperture.

8. The fluid contactor element of claim 3 wherein said sponge inner-member has a strip which spirals within said outer-member.

9. The fluid contactor element of claim 1 wherein said tough resilent outer cylindrical-shaped member defines a multiplicity of apertures.

10. The fluid contactor element of claim 9 wherein the material removed to form said apertures remains as excess material around said apertures on the inside of said outer member to provide points for the formation of liquid droplets, and to prevent liquid from running along the inside wall of said outer member.

11. The fluid contactor of claim 9 wherein the cross-section of the inside and outside walls of said substantially cylindrical shaped outer member is scalloped having crests and troughs.

12. The fluid contactor element of claim 11 wherein said sponge inner-member has a scalloped-cylindrically shaped cross-section.

13. The fluid contactor element of claim 1 or 2 wherein said outer structure is oval or egg-shaped.

14. The fluid contactor element of claim 1 wherein said outer member is oval or egg-shaped, and wherein said inner-member comprises a multiplicity of plates extending between the walls of said oval-shaped member.

15. The fluid contactor elements of claims 1, 2, or 14 wherein a multiplicity of said elements are used to pack a gas/liquid packing tower.

16. A tough and abrasive resistant fluid contactor element comprising a tough and abrasive resistant substantially cylindrically shaped member having a longitudinal axis, and wherein a cross-section perpendicular to said longitudinal axis through said substantially cylindrically shaped member has inside and outside walls, each of which are scalloped having a multiplicity of crests and a multiplicity of troughs.

17. The contactor of claim 16 wherein said crests are wider than said troughs such that said crests will not reach the bottom of said troughs.

18. The contactor of claim 17 wherein apertures are defined in the troughs and the waste material from the apertures remain next to the inside of the hole such that a projection which aids in drop formation results.

19. The contactor of claims 16, 17 or 18 wherein said fluid contactor element is made from a material selected from the group consisting of plastics and ceramics.

20. The contactor of claim 19 and including at least two inner support ribs extending from said walls toward the center of said contactor.

21. The contactor of claim 20 wherein said ribs include indentations to facilitate the formation of liquid droplets.

* * * * *